(12) United States Patent
Johnson et al.

(10) Patent No.: US 10,874,443 B2
(45) Date of Patent: Dec. 29, 2020

(54) INTERNAL FIXATION DEVICES WITH ROTATABLE SCREW LOCKS

(71) Applicant: ZAVATION MEDICAL PRODUCTS LLC, Flowood, MS (US)

(72) Inventors: Jeffrey Johnson, Flowood, MS (US); John Lawrence Walker, Madison, MS (US); John Franklin Cummins, Kosciusko, MS (US)

(73) Assignee: Zavation Medical Products, LLC, Flowood, MS (US)

( * ) Notice: Subject to any disclaimer, the term of this patent is extended or adjusted under 35 U.S.C. 154(b) by 329 days.

(21) Appl. No.: 15/926,363

(22) Filed: Mar. 20, 2018

(65) Prior Publication Data

US 2018/0271571 A1 Sep. 27, 2018

Related U.S. Application Data

(60) Provisional application No. 62/474,768, filed on Mar. 22, 2017.

(51) Int. Cl.
*A61B 17/80* (2006.01)
*A61B 17/70* (2006.01)

(52) U.S. Cl.
CPC ...... *A61B 17/8042* (2013.01); *A61B 17/7059* (2013.01)

(58) Field of Classification Search
CPC .................................................. A61B 17/8042
See application file for complete search history.

(56) References Cited

U.S. PATENT DOCUMENTS

| 8,652,182 B1 | 2/2014 | Walker et al. | |
| 2002/0004683 A1* | 1/2002 | Michelson | A61F 2/4455 623/17.16 |
| 2012/0158068 A1* | 6/2012 | Humphreys | A61B 17/8042 606/286 |

* cited by examiner

*Primary Examiner* — Olivia C Chang
(74) *Attorney, Agent, or Firm* — Olive Law Group PLLC; Ronald A. Rudder (57) ABSTRACT

Internal fixation devices are provided that include a plate having a rotatable screw lock mounted in a recess of the plate. The screw lock has a lock head including a laterally extending flange that has an outer edge that is below the upper surface of the plate. In a locked position, a portion of the upper surface of the plate covers at least a part of the lock head to reduce the likelihood of the screw lock being pushed off the plate. Further, in a locked position, the laterally extending flange obstructs passage of a screw through a corresponding screw hole. Such obstruction hinders screw migration.

7 Claims, 7 Drawing Sheets

INTERNAL FIXATION DEVICES WITH ROTATABLE SCREW LOCKS

CROSS-REFERENCE TO RELATED APPLICATIONS

The present application claims priority to U.S. Provisional Application No. 62/474,768 filed on Mar. 22, 2017, which is incorporated by reference in its entirety.

TECHNICAL FIELD

The present disclosure relates to internal fixation devices, such as bone plates, with rotatable screw locks.

BACKGROUND

Internal fixation devices, such as plates, pins, rods, wires and screws, are often used to stabilize and join bones. For example, internal fixation devices can be used to facilitate healing of bone fractures or to fuse adjacent vertebral bodies of a patient's spinal column. In the case of internal fixation devices that are plates, the plates are placed against adjacent bone tissue and screws are inserted through screw holes of the plates into the adjacent bone tissue to anchor the plates into proper position.

In some circumstances, the screws can "back-out" of the underlying bone. To address this problem, a bone plate can include a screw lock that is rotated over the screw head of the screw. However, the screws can back out of the bone tissue to such an extent that the screw lock is flexed upwards. Such flexing can damage the screw lock resulting in failure of the internal fixation system. In addition, a practitioner can only visually ascertain when such a rotatable screw lock has been sufficiently rotated to adequately block the underlying bone screw from backing out.

SUMMARY

The present disclosure generally relates to internal fixation devices. In an embodiment, an internal fixation device comprises a plate having a body with an upper surface and a bottom surface. The plate further includes a screw hole extending through the upper and bottom surfaces of the plate body. The plate also includes a recess in fluid communication with the screw hole and defined by a retention portion of the upper surface of the plate body, a lower surface of the plate body, and a discontinuous wall having a first side separate by a gap from a second side. The second side of the discontinuous wall is contiguous with the retention portion of the upper surface. The gap is in fluid communication with the screw hole. The internal fixation device also includes a rotatable screw lock mounted in the recess of the plate body. The screw lock has a lock head including a laterally extending flange that has an outer edge that is below the upper surface of the plate body. In a locked position, (a) the retention portion of the upper surface covers at least a part of the lock head to reduce the likelihood of the screw lock being pushed off the plate and (b) at least part of the laterally extending flange is within the gap to obstruct passage of a screw through a corresponding screw hole. Such obstruction hinders screw migration such as, for example, the screw backing out of the underlying bone. This, in turn, reduces the risk of device separation or failure of the internal fixation system.

In an embodiment, an internal fixation device comprises a plate having a body with an upper surface and a bottom surface. The plate includes a first screw hole and a second screw hole extending through the upper and bottom surfaces of the plate body. The plate also includes a recess in fluid communication with the first and second screw holes. The recess is defined by a retention portion of the upper surface of the plate body, a lower surface of the plate body, and a discontinuous wall comprising a first gap in fluid communication with the first screw hole and a second gap in fluid communication with the second screw hole. The internal fixation device further comprises a rotatable screw lock mounted in the recess of the plate body. The lock head of the screw lock includes a single laterally extending flange that has an outer edge that is below the upper surface of the plate body. In a locked position, a first part of the single laterally extending flange is within the first gap, a second part of the single laterally extending flange is within the second gap, and part of the lock head is covered by the retention portion of the upper surface of the plate body. The first and second parts of the single extending flange are within the first and second gaps respectively to obstruct passage of a screw from a corresponding screw hole. The retention portion sufficiently covers part of the lock head to minimize the likelihood that the screw lock is pushed off the plate.

In another embodiment, an internal fixation device comprises a plate having a body with an upper surface and a bottom surface. The plate includes a first screw hole and a second screw hole extending through the upper and bottom surfaces of the plate body. The plate also includes a recess in fluid communication with the first and second screw holes. The recess is defined by a retention portion of the upper surface of the plate body, a lower surface of the plate body, and a discontinuous wall comprising a first gap in fluid communication with the first screw hole and a second gap in fluid communication with the second screw hole. The internal fixation device further comprises a rotatable screw lock mounted in the recess of the plate body. The screw lock has a lock head including first and second laterally extending flanges that each have outer edges that are below the upper surface of the plate body. In a locked position, the first flange is at least partially within the first gap, the second flange is at least partially within the second gap, and part of the lock head is covered by the retention portion of the upper surface of the plate body. The first and second flanges are sufficiently within the first and second gaps respectively to obstruct passage of a screw from a corresponding screw hole. The retention portion sufficiently covers part of the lock head to minimize the likelihood that the screw lock is pushed off the plate.

DETAILED DESCRIPTION

As used herein with respect to a described element, the terms "a," "an," and "the" include at least one or more of the described element unless otherwise indicated. Further, the term "or" refers to "and/or" including combinations thereof unless otherwise indicated. When an element is referred to as being "on," "attached" to, "connected" to, "coupled" with, "contacting," in "fluid communication" with, etc., another element, it can be directly on, attached to, connected to, coupled with, contacting, or in fluid communication with the other element or intervening elements may also be present. In contrast, when an element is referred to as being, for example, "directly on," "directly attached" to, "directly connected" to, "directly coupled" with, "directly contacting," or in "direct fluid communication" with another element, there are no intervening elements present. Reference to an element that is disposed "adjacent" another element may have portions that overlap or underlie the adjacent element. In an "unlocked position" of an internal fixation device described herein, a screw lock does not obstruct passage of a screw through a screw hole of a plate of the internal fixation device. In a "locked position," the screw lock obstructs passage of the screw through the screw hole of the plate of the internal fixation device and part of the lock head of the screw lock is covered by a portion of the upper surface of the plate.

Figure 1:
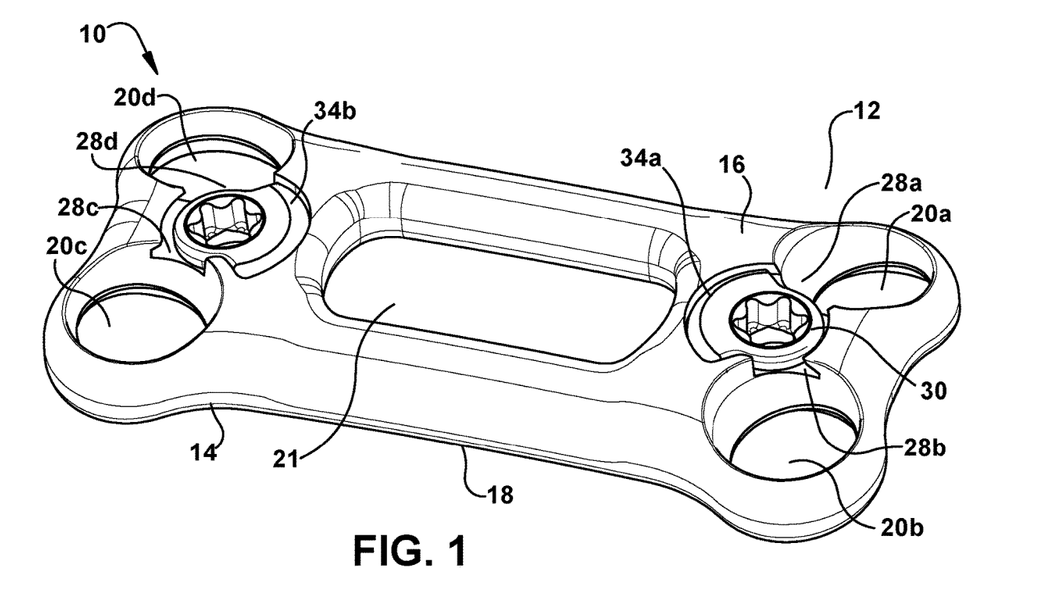
FIG. 1 is a perspective view of an internal fixation device according to an embodiment of the present disclosure.
Figure 2:
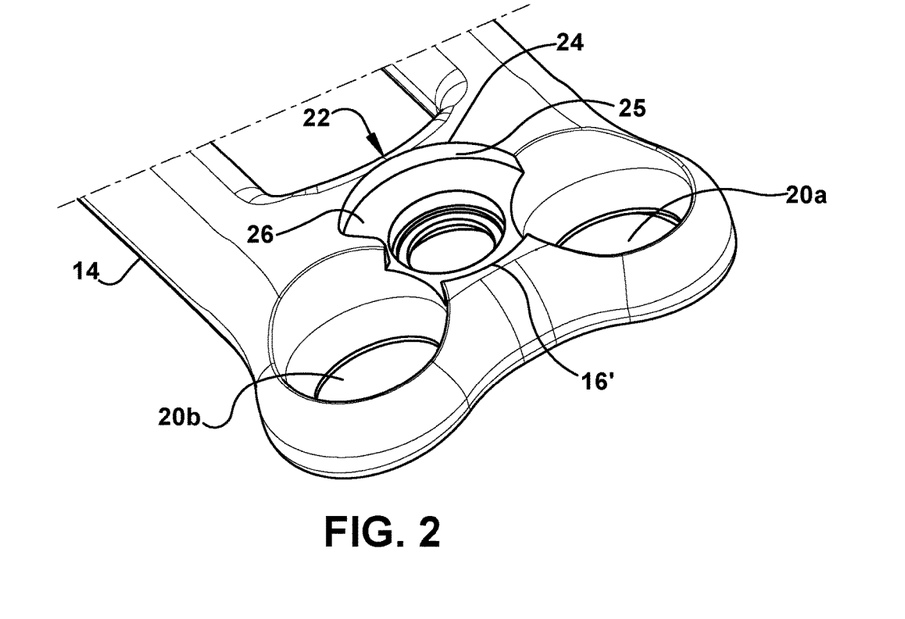
FIG. 2 is a partial perspective view of a plate of an internal fixation device according to an embodiment of the present disclosure. A screw lock of the internal fixation device is omitted for the purposes of clarity.
Figure 3:
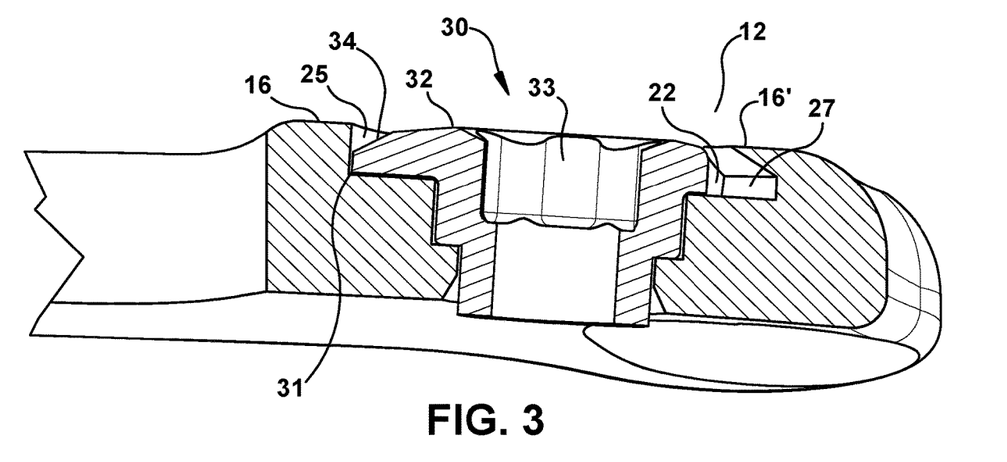
FIG. 3 is partial cross-sectional view of an internal fixation device in an unlocked position according to an embodiment of the present disclosure.
Figure 4:
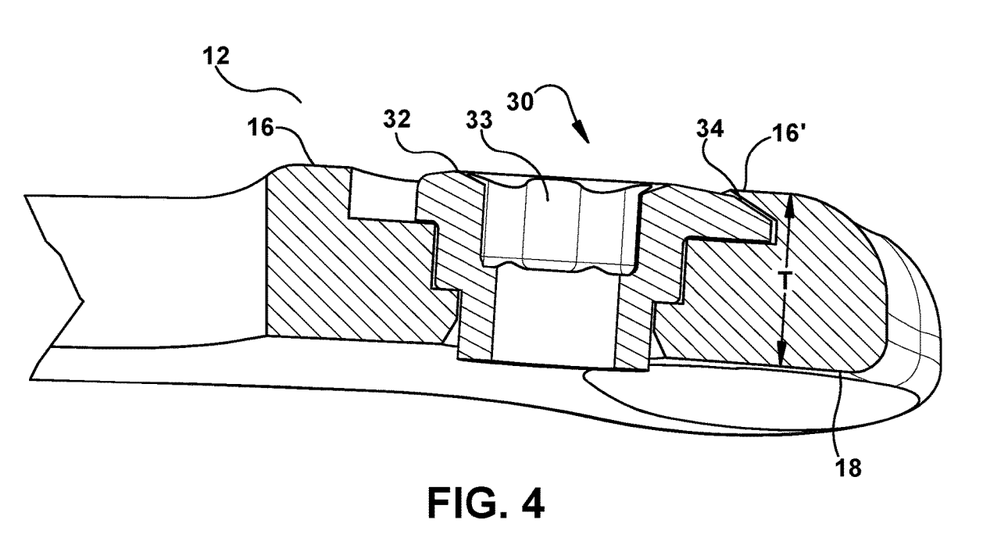
FIG. 4 is a partial cross-sectional view of the internal fixation device of FIG. 3 in a locked position.

The present disclosure generally relates to internal fixation systems. Referring to FIG. 1, in an embodiment, an internal fixation device 10 comprises a plate 12 having a body 14 with an upper surface 16 and a bottom surface 18. A screw hole 20 extends through upper surface 16 and bottom surface 18 of plate body 14. Referring also to FIGS. 2-4, plate 12 further includes a recess 22 in fluid communication with screw hole 20. Recess 22 is defined by a retention portion 16' of upper surface 16 of plate body 14 adjacent to screw hole 20, a discontinuous wall 24, and a lower surface 26 of plate body 14. Wall 24 has a first side 25 and a second side 27. As seen in FIGS. 3 and 4, second side 27 is contiguous with retention portion 16'. First side 25 and second side 27 are separated by a gap 28 that is in fluid communication with screw hole 20. Internal fixation device 10 further includes a rotatable screw lock 30 mounted in recess 22.

As seen in FIGS. 3 and 4, screw lock 30 has a lock head 32 including a laterally extending flange 34 (also referred to herein as a "flange") that has an outer edge 31 that is below upper surface 16 of plate body 14 in a locked position (depicted in FIG. 4) and preferably also in an unlocked position (depicted in FIG. 3). In certain embodiments, the entire flange is below the upper surface of the plate body. The flange is configured and dimensioned to obstruct passage of a bone screw through a corresponding screw hole in a locked position. Lock head 32 defines a socket 33 to accept a driver to rotate the screw lock. The socket can have the same configuration and dimensions of a bone screw used with the internal fixation device so that the same driver can be used to rotate the screw lock and the bone screw. Referring back to FIG. 1, in certain embodiments, plate body defines a window 21 providing the practitioner with a view of the disc space and any bone graft material inserted into the disc space.

As illustrated in FIG. 1, an internal fixation device can comprise a plurality of screw holes, a plurality of recesses that are each in fluid communication with corresponding ones of the plurality of screw holes, a plurality of rotatable screw locks that are each mounted in a corresponding one of the plurality of recesses, and a plurality of gaps each in fluid communication with a corresponding one of the plurality of screw holes. Each of the plurality of rotatable screw locks can have a single laterally extending flange or a plurality of laterally extending flanges.

Figure 5:
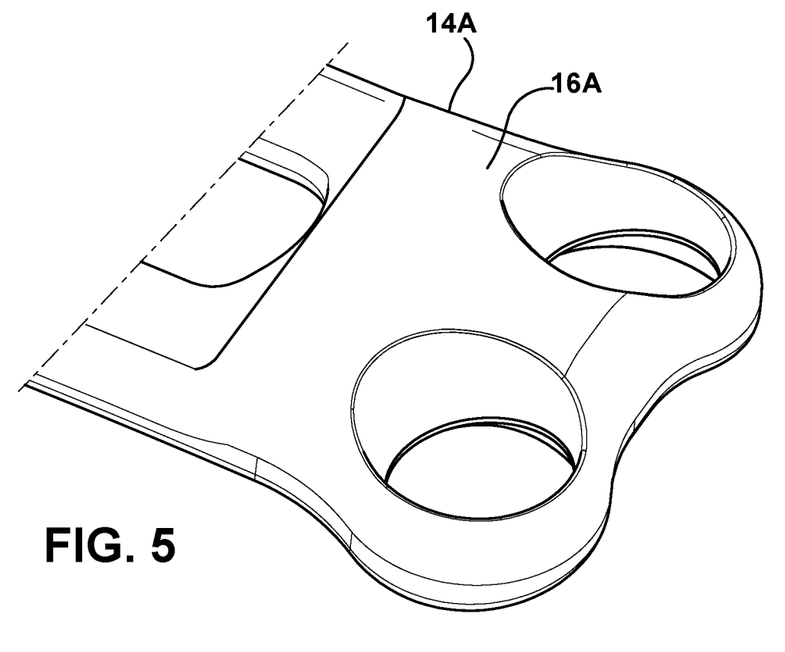
FIG. 5 is partial perspective view of a plate body of an internal fixation device before a recess has been cut into the plate body.
Figure 6:
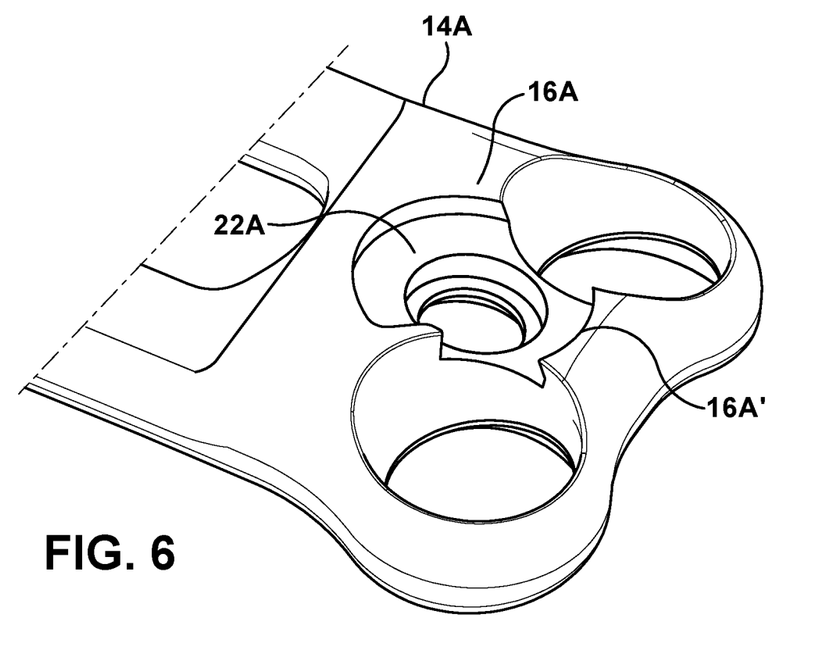
FIG. 6 is a partial perspective view of the plate body of FIG. 5 after the recess has been cut into the plate body.

As stated above, the laterally extending flange of a screw lock has an outer edge that is below the upper surface of the plate body. In other words, the outer edge of the laterally extending flange does not protrude or extend above the upper surface of the plate body. Further, the retention portion of the upper surface of the plate body is part of/defined by the upper surface of the plate body and does not protrude or extend above the upper surface of the plate body. This is clearly illustrated in FIGS. 5 and 6. FIG. 5 illustrates a plate body 14A before a recess has been cut into the upper surface 16A of plate body 14A. FIG. 6 illustrates plate body 14A after a recess 22A has been cut into upper surface 16A of plate body 14A. As seen by a comparison of FIGS. 5 and 6, upper surface 16A defines retention portion 16A' and is not a protrusion that extends above upper surface 16A.

As seen in FIGS. 3 and 4, outer edge 31 of laterally extending flange 34 and retention portion 16' do not increase the overall thickness T of plate 12 as measured from bottom surface 18 to upper surface 16 since the outer edge of laterally extending flange 34 and retention portion 16' do not protrude above upper surface 16. As such, when implanted in a patient's body, the internal fixation device is less likely to irritate adjacent tissue that contacts the internal fixation device.

Figure 7:
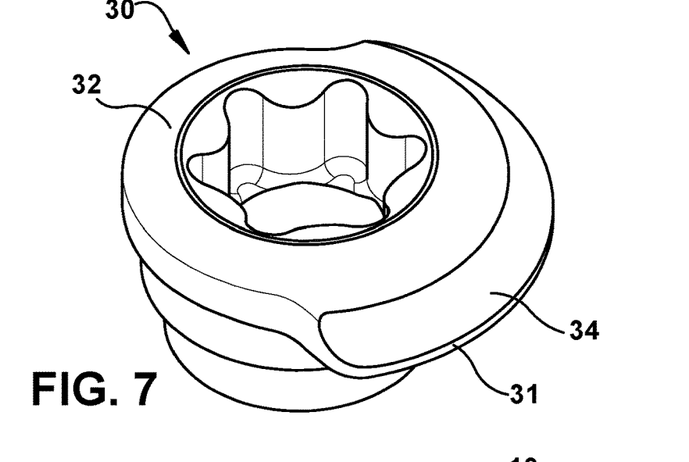
FIG. 7 is a perspective view of a screw lock of an internal fixation device according to an embodiment of the present disclosure.

Referring to FIG. 7, laterally extending flange 34 of screw lock 30 does not extend about the entire circumference of lock head 32 but only partially extends about the circumstance of lock head 32. As such, laterally extending flange 34 does not obstruct passage of a screw (illustrated in FIG. 8, for example) through a screw hole of the plate in an unlocked position. The laterally extending flange can be a single flange as illustrated FIG. 7 or a plurality of flanges as illustrated in FIGS. 12-15.

Figure 8:
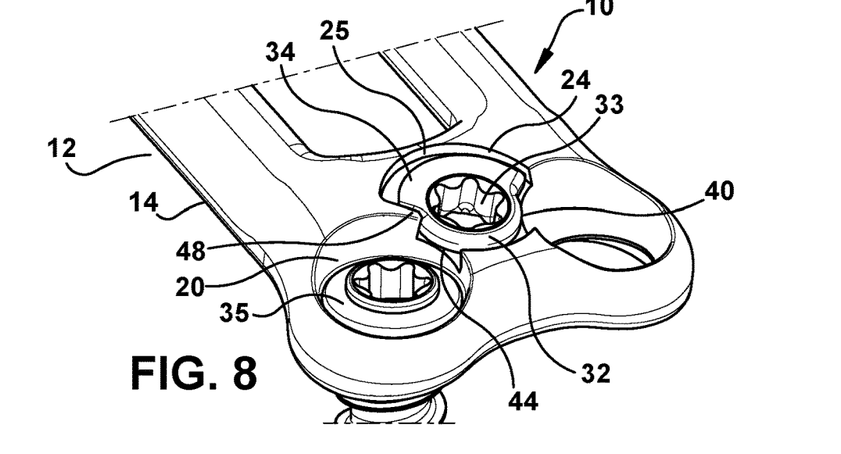
FIG. 8 is a partial perspective view of an internal fixation device in an unlocked position according to an embodiment of the present disclosure.
Figure 9:
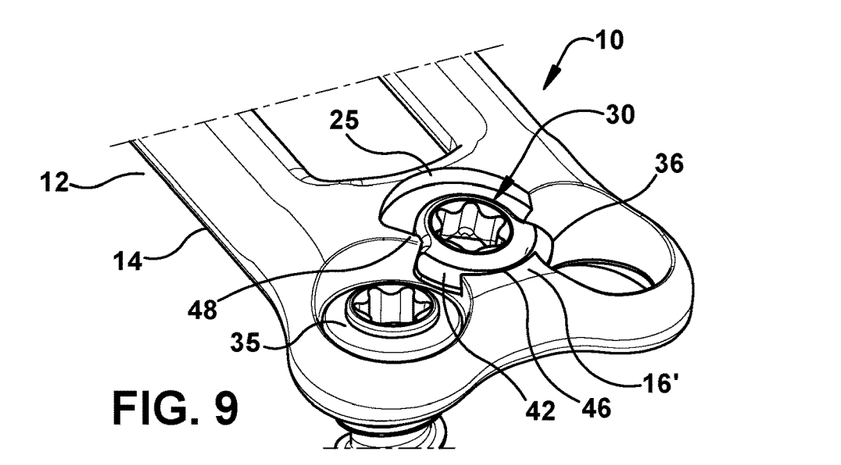
FIG. 9 is a partial perspective view of the internal fixation device of FIG. 8 in a locked position.
Figure 10:
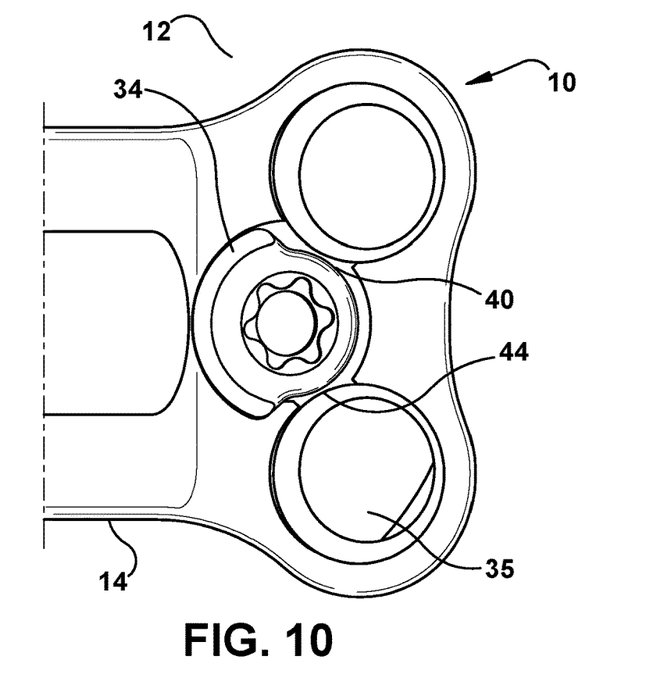
FIG. 10 is a top view of an internal fixation device in an unlocked position according to an embodiment of the present disclosure.
Figure 11:
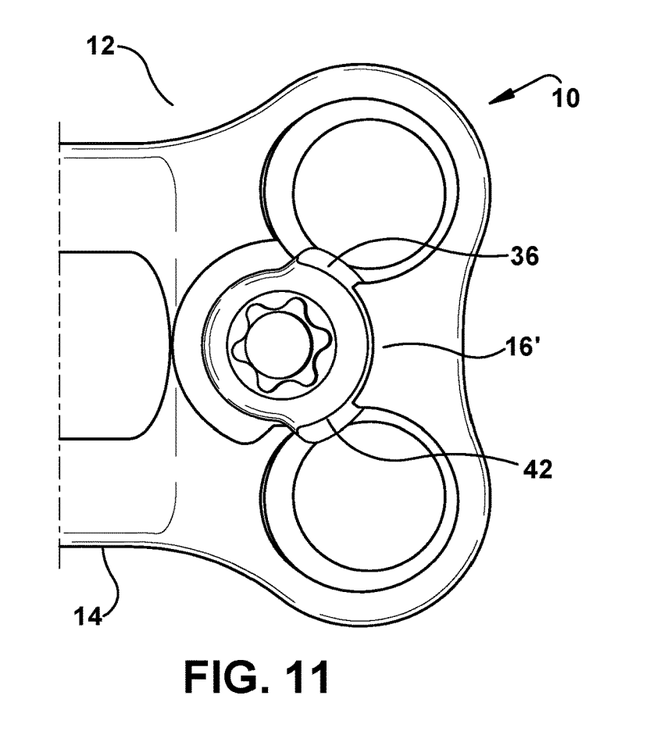
FIG. 11 is top view of the internal fixation device of FIG. 10 in a locked position.
Figure 15:
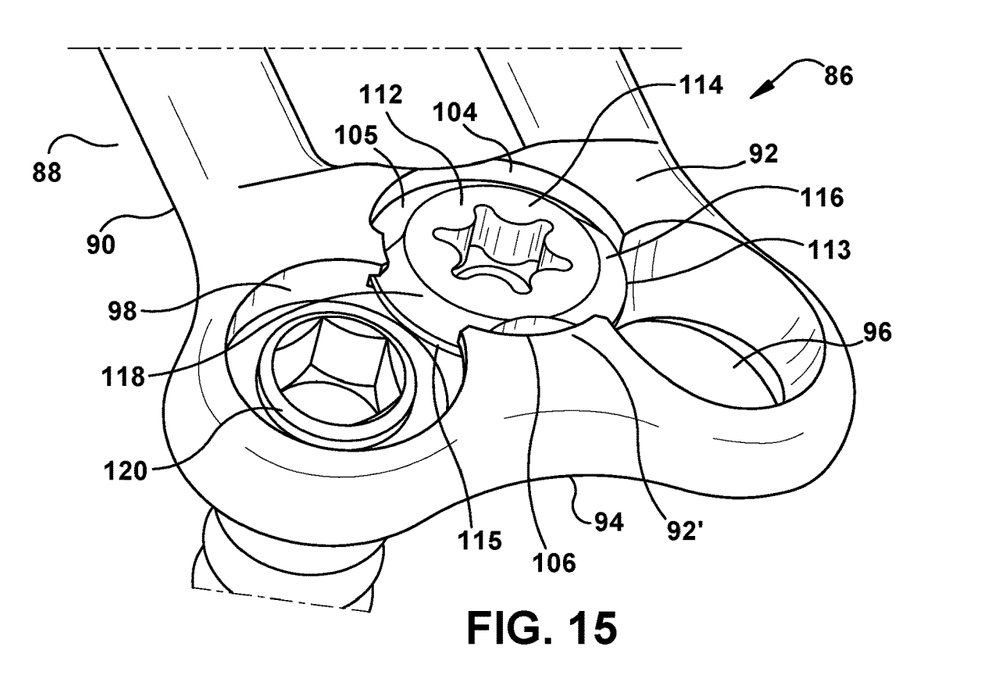
FIG. 15 is a partial perspective view of the internal fixation device of FIG. 14 in a locked position.

FIGS. 8-11 depict a laterally extending flange that is a single flange. In an unlocked position, flange 34 faces first side 25 of wall 24 as seen in FIGS. 8 and 10 and does not obstruct passage of a screw 35 through screw hole 20. A driver can be inserted into a socket 33 of lock head 32 to rotate screw lock 30 into a locked position, as seen in FIGS. 9 and 11, such that a first part 36 of flange 34 is a within a first gap 40 of wall 24, a second part 42 of flange 34 is within a second gap 44 of wall 24, and another part 46 of lock head 32 (such as, for example, a part of flange 34) is covered by retention portion 16' of upper surface 16 of plate body 14 as seen in FIGS. 9 and 11. First and second parts 36 and 42 of flange 34 are within first and second gaps 40 and 44 to obstruct passage of a bone screw from a corresponding screw hole. Part 46 may be a continuous part of flange 34 or two spaced parts as illustrated in FIG. 15, described below, so long as the retention portion covers a sufficient part of the lock head of the screw lock to reduce the likelihood of the screw lock being pushed off the plate in a locked position.

First side 25 of wall 24 can terminate in an abutment 48 extending radially inward and an end of flange 34 contacts abutment 48 in a locked position and preferably also an unlocked position as illustrated in FIGS. 8 and 9. In a locked position, abutment 48 stops further rotation of screw lock 30 and provides a tactile indication to the practitioner that the screw lock is properly placed such that the first and second parts 36 and 42 of flange 34 are within first and second gaps 40 and 44, respectively.

As stated above, the laterally extending flange of a screw lock can be a plurality of laterally extending flanges as illustrated in FIGS. 12-15, which are partial perspective views of internal fixation devices. The portion of the lock head between adjacent flanges does not laterally extend past the adjacent flanges so that such portion does not obstruct passage of bone screw in an unlocked position.

Figure 12:
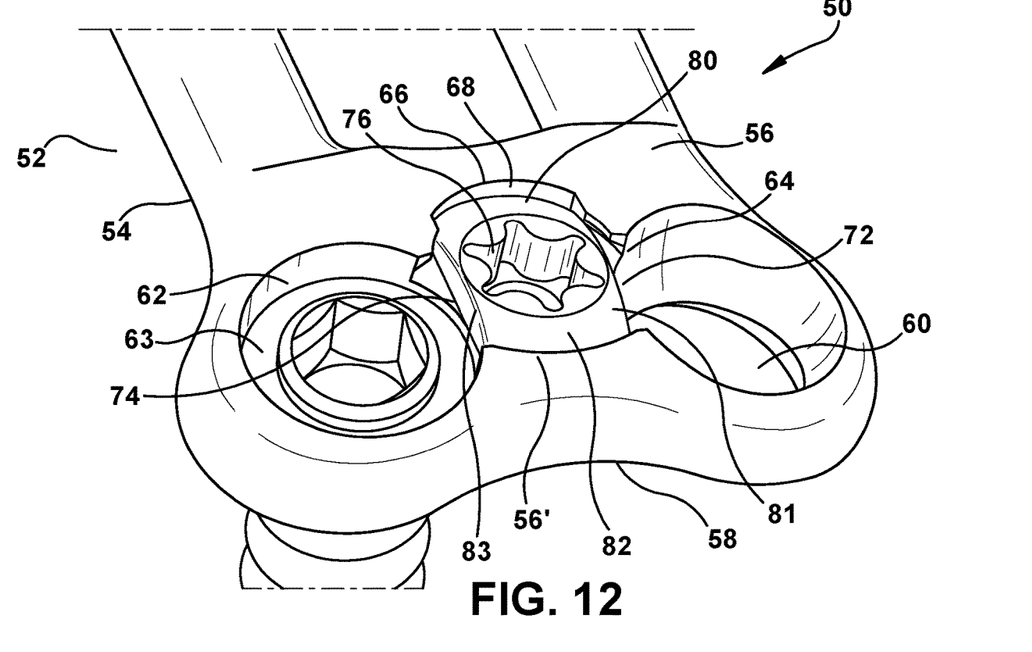
FIG. 12 is a partial perspective view of an internal fixation device in an unlocked position according to an embodiment of the present disclosure.
Figure 13:
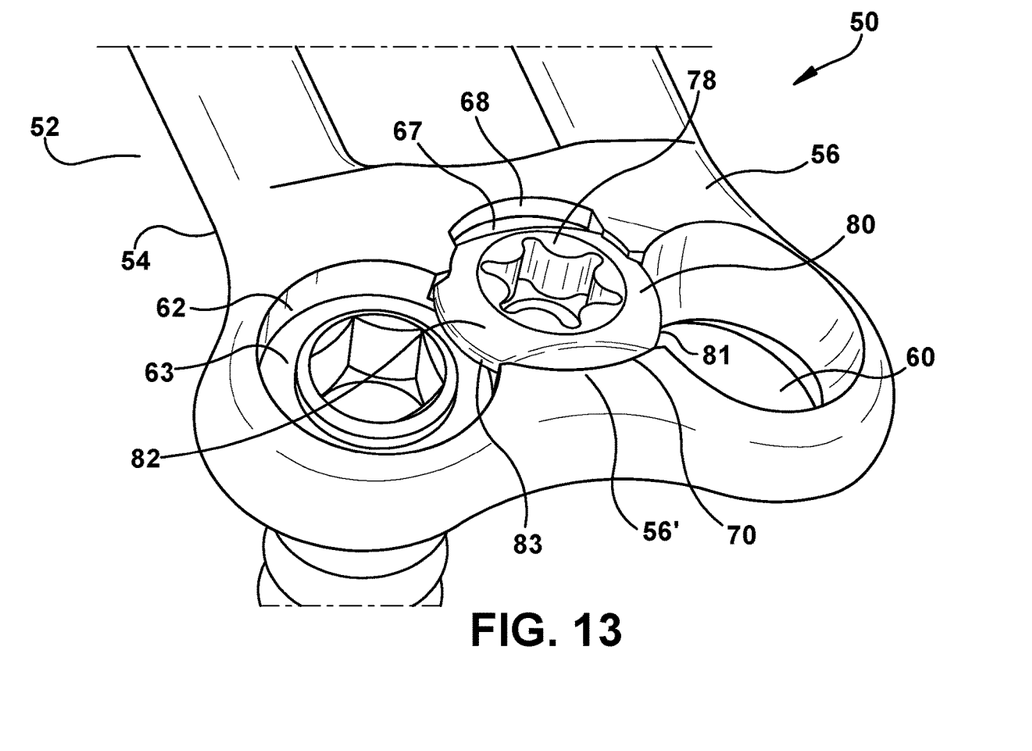
FIG. 13 is a partial perspective view of the internal fixation device of FIG. 12 in a locked position.

Referring to FIGS. 12 and 13, in an embodiment, an internal fixation device 50 comprises a plate 52 having a body 54 with an upper surface 56 and a bottom surface 58. A first screw hole 60 and a second screw hole 62 extend through upper surface 56 and bottom surface 58. Plate 52 further includes a recess 64 in fluid communication with first screw hole 60 and second screw hole 62. Recess 64 is defined by a retention portion 56' of upper surface 56 of plate body 54 adjacent to screw holes 60 and 62, a discontinuous wall 66, and a lower surface 67 of plate body 54. Wall 66 has a first side 68, a second side 70 contiguous with retention portion 56', a first gap 72 in fluid communication with first screw hole 60, and a second gap 74 in fluid communication with second screw hole 62. Internal fixation device 50 further includes a rotatable screw lock 76 having a lock head 78 including a first flange 80 and a second flange 82. First and second flange 80 and 82 each has a respective outer edge 81 and 83 that are below upper surface 56 of plate body 54. FIGS. 12 and 13 illustrate only two flanges, but the lock head can include more than two flanges depending on how many screw holes are adjacent to the recess of the plate. In the embodiment illustrated in FIGS. 12 and 13, first flange 80 and second flange 82 are on opposite sides on lock head 78.

In an unlocked position depicted in FIG. 12, first flange 80 faces first side 68 of wall 66 and second flange 82 faces second side 70 of wall 66. As seen in FIG. 12, the portions 81 and 83 of lock head 78 between first flange 80 and second flange 82 do not laterally extend beyond flanges 80 and 82 so to not obstruct passage of a bone screw 63 through corresponding second screw hole 62 and a bone screw (not shown) through corresponding first screw hole 60. In this embodiment, a practitioner rotates the screw lock approximately 90° (e.g. requiring only an approximately half turn of the driver used to rotate the screw lock) to place the screw lock in a locked position illustrated in FIG. 13. Further, because the first side of the discontinuous wall does not terminate in an abutment extending radially inward, the screw lock can be rotated in a clockwise or counter-clockwise direction. In a locked position, first flange 80 is at least partially within first gap 72 of wall 66, second flange 82 is at least partially within second gap 74 of wall 66, and part of lock head 78 (such as parts of both first and second flanges 80 and 82) is covered by retention portion 56' of upper surface 56 of plate body 54. First and second flanges 80 and 82 are sufficiently within first and second gaps 72 and 74 respectively to obstruct passage of a screw through a corresponding screw hole.

As with other embodiments, the internal fixation device can comprise a plurality of screw holes, a plurality of recesses that are each in fluid communication with corresponding ones of the plurality of screw holes, a plurality of rotatable screw locks that are each mounted in a corresponding one of the plurality of recesses, and a plurality of gaps each in fluid communication with a corresponding one of the plurality of screw holes.

Figure 14:
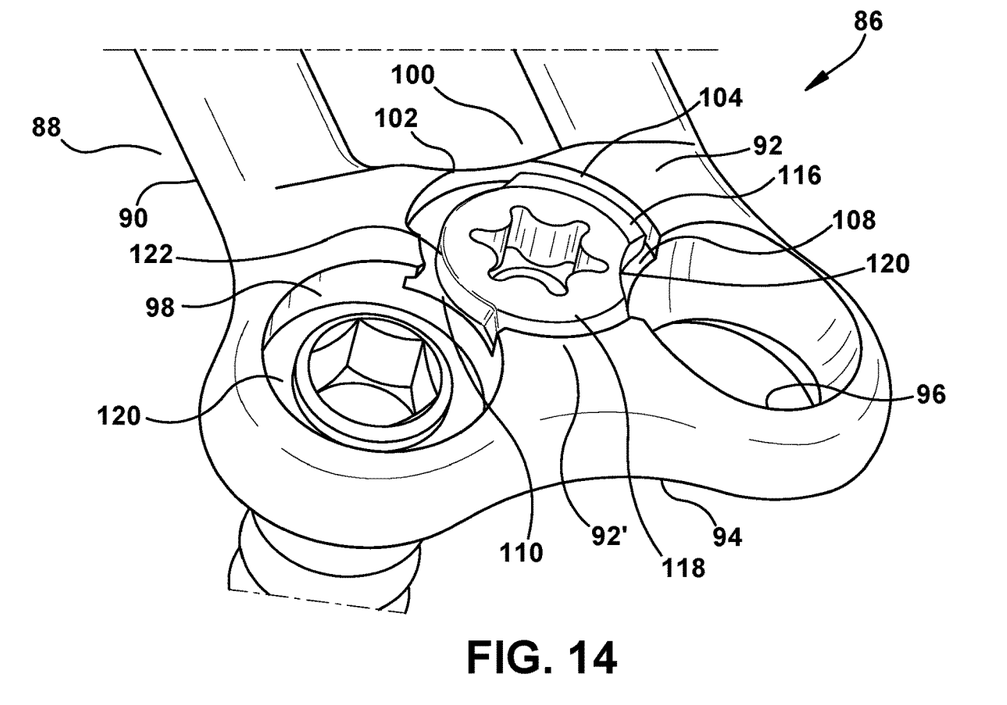
FIG. 14 is a partial perspective view of an internal fixation device in an unlocked position according to an embodiment of the present disclosure.

Referring to FIGS. 14 and 15, in another embodiment, an internal fixation device 86 comprises a plate 88 having a body 90 with an upper surface 92 and a bottom surface 94. A first screw hole 96 and a second screw hole 98 extend through upper surface 92 and bottom surface 94. Plate 88 further includes a recess 100 in fluid communication with first screw hole 96 and second screw hole 98. Recess 100 is defined by a retention portion 92' of upper surface 92 of plate body 90 adjacent to screw holes 96 and 98, a discontinuous wall 102, and a lower surface 105 of plate body 90. Wall 102 has a first side 104, a second side 106 contiguous with retention portion 92', a first gap 108 in fluid communication with first screw hole 96, and a second gap 110 in fluid communication with second screw hole 98. Internal fixation device 86 further includes a rotatable screw lock 112 having a lock head 114 including a first flange 116 and a second flange 118. First and second flange 116 and 118 each has a respective outer edge 113 and 115 that are below upper surface 92 of plate body 90. FIGS. 14 and 15 illustrate only two flanges, but the lock head can include more than two flanges depending on how many screw holes are adjacent to the recess of the plate.

In an unlocked position depicted in FIG. 14, first flange 116 faces first side 104 of wall 102 and second flange 118 faces second side 106 of wall 102. As seen in FIG. 14, the portions 120 and 122 of screw head 114 between first flange 116 and second flange 118 do not laterally extend beyond the flanges 116 and 118 so to not obstruct passage of a bone screw 120 through corresponding second screw hole 98 and a bone screw (not shown) through corresponding first screw hole 96. Portion 120 can have a concave surface to ensure that lock head 114 does not obstruct passage of a bone screw through corresponding first screw hole 96 in an unlocked position. In this embodiment, a practitioner rotates the screw lock approximately 45° (e.g. requiring only an approximately quarter turn of the driver used to rotate the screw lock) to place the screw lock in a locked position illustrated in FIG. 15. In a locked position, first flange 116 is at least partially within first gap 108 of wall 102, second flange 118 is at least partially within second gap 110 of wall 102 and part of lock head 114 (such as, for example, parts of both first and second flanges 116 and 118) are covered by retention portion 92' of upper surface 92 of plate body 90. The parts of first and second flanges 116 and 118 that are covered by retention portion 92' can be spaced from one another as illustrated in FIG. 15, so long as retention portion 16' covers a sufficient part of the screw lock to reduce the likelihood that the screw lock is pushed off plate 88. First and second flanges 116 and 118 are sufficiently within first and second gaps 108 and 110 respectively to obstruct passage of a screw through a corresponding screw hole.

As with other embodiments, the internal fixation device can comprise a plurality of screw holes, a plurality of recesses that are each in fluid communication with corresponding ones of the plurality of screw holes, a plurality of rotatable screw locks that are each mounted in a corresponding one of the plurality of recesses, and a plurality of gaps each in fluid communication with a corresponding one of the plurality of screw holes.

Internal fixation devices as disclosed herein can be used for bone fractures, bone fusion, and other medical procedures requiring fixation of tissue. Such devices can be configured to be implanted on the spinal column, such as, for example, the cervical spinal region or the lumbar spinal region. The devices also can be configured as occipito-cervico-thoracic fixation devices to treat pathologies of the occipitocervical junction, and the posterior cervical and upper thoracic spine. Alternatively, internal devices can be configured to stabilize skull fractures, facial fractures, or craniomaxillofacial fractures. The internal fixation devices can be left in place in the patient or removed after the bone has fused.

Each of the disclosed aspects and embodiments of the present disclosure may be considered individually or in combination with other aspects, embodiments, and variations of the invention. Further, while certain features of embodiments of the present disclosure may be shown in only certain figures, such features can be incorporated into other embodiments shown in other figures.

What is claimed is:

1. An internal fixation device comprising
a plate having a plate body with an upper surface and a bottom surface and comprising:
   a screw hole extending through the upper and bottom surfaces of the plate body;
   a recess in fluid communication with the screw hole and defined by a retention portion of the upper surface of the plate body, a lower surface of the plate body, and a discontinuous wall having a first side separated by a gap from a second side, the gap in fluid communication with the screw hole; and
   a rotatable screw lock mounted in the recess of the plate body and having a lock head including a single laterally extending flange having an outermost edge that is below the upper surface of the plate body,
wherein in a locked position (a) the retention portion of the upper surface of the plate body adjacent to the gap covers a first radial part of the outermost edge of the single laterally extending flange of the lock head and (b) a second radial part of the outermost edge of the single laterally extending flange of the lock head is within the gap and covers at least part of the screw hole, and
wherein the single laterally extending flange has a circular edge of a constant diameter comprising the outermost edge, and the circular edge of the constant diameter extends along the outermost edge of the first radial part and the second radial part.

2. The internal fixation device of claim 1, wherein the first side of the discontinuous wall terminates in an abutment extending radially inward, and the single laterally extending flange contacts the abutment in a locked position.

3. The internal fixation device of claim 1, wherein the single laterally extending flange contacts the abutment in an unlocked position.

4. The internal fixation device of claim 1, wherein the screw hole comprises a plurality of screw holes, the recess comprises a plurality of recesses each in fluid communication with corresponding ones of the screw holes, the rotatable screw lock comprises a plurality of rotatable screw locks each mounted in a corresponding one of the plurality of recesses, and the gap comprises a plurality of gaps each in fluid communication with a corresponding one of the plurality of screw holes.

5. The internal fixation device of claim 1, wherein the screw lock comprises a socket configured to accept a driver to rotate the screw lock.

6. An internal fixation device comprising
a plate having a plate body with an upper surface and a bottom surface and comprising:
   a first screw hole and a second screw hole extending through the upper and bottom surfaces of the plate body;
   a recess in fluid communication with the first and second screw holes, the recess defined by a retention portion of the upper surface of the plate body, a lower surface of the plate body, and a discontinuous wall comprising a first gap in fluid communication with the first screw hole and a second gap in fluid communication with the second screw hole; and
a rotatable screw lock mounted in the recess of the plate body and having a lock head including a single laterally extending flange having an outermost edge that is below the upper surface of the plate body,
wherein in a locked position, a first radial part of the outermost edge of the single laterally extending flange is within the first gap, a second radial part of the outermost edge of the single laterally extending flange is within the second gap, and a third radial part of the outermost edge of the single laterally extending flange is covered by the retention portion of the upper surface of the plate body, and
wherein the single laterally extending flange has a circular edge of a constant diameter comprising the outermost edge, and the circular edge of the constant diameter extends along the outermost edge of the first radial part, the second radial part, and the third radial part.

7. The internal fixation device of claim 6, wherein the third radial part of the lock head that is covered by the retention portion is adjacent the first radial part and is adjacent the second radial part of the single laterally extending flange.

* * * * *